(12) United States Patent
Onichtchenko

(10) Patent No.: US 6,387,633 B1
(45) Date of Patent: May 14, 2002

(54) METHOD FOR IDENTIFYING UNSTABLE GENES

(75) Inventor: Anatoli Onichtchenko, Laval (CA)

(73) Assignee: Supratek Pharma, Inc., Dorval (CA)

( * ) Notice: Subject to any disclaimer, the term of this patent is extended or adjusted under 35 U.S.C. 154(b) by 0 days.

(21) Appl. No.: 09/854,271

(22) Filed: May 11, 2001

(51) Int. Cl.⁷ .................................................. C12Q 1/68
(52) U.S. Cl. ............................................................ 435/6
(58) Field of Search ............................................. 435/6

(56) References Cited

PUBLICATIONS

Mariam S. Grigorian et al, The mts1 gene and control of tumor metastasis, Gene 135, 1993, 229–238.*

* cited by examiner

*Primary Examiner*—Terry McKelvey
(74) *Attorney, Agent, or Firm*—Gibbons, Del Deo, Dolan, Griffinger & Vecchione

(57) ABSTRACT

The present invention provides a method for the generation and identification cell lines that posses genetically unstable genes. More specifically, the present invention provides a method for detecting genes associated in genetic alterations by using specific genes capable of inducing genetic instability such as metastasin 1 gene and their protein products.

6 Claims, No Drawings

METHOD FOR IDENTIFYING UNSTABLE GENES

FIELD OF INVENTION

The present invention relates to a method for identifying genetic instability and screening for genes involved in genetic alterations by using genes that are capable of inducing genetic instability. More specifically, the present invention provides a method for generating genetically unstable cell lines by using the human metastasin 1.

BACKGROUND OF THE INVENTION

Neoplastic cells typically possess numerous lesions, which may include sequence alterations such as point mutations, small deletions, insertions and/or gross structural abnormalities in one or more chromosomes such as large-scale deletions, rearrangements, or gene amplifications (Hart and Saini, 1992 *Lancet*, 333:1453–61; Seshadri et al., 1989 *Int. J. Cancer*, 43:270–72. Based upon this general observation, it has been suggested that cancer cells are genetically unstable and that acquisition of genomic instability may represent an early step in the process of carcinogenesis and a general feature of many human tumors (Liotta et al., 1991 *Cell*, 64:327–36. The ensuing genetic instability drives tumor progression by generating mutations in oncogenes and tumor-suppressor genes, which leads to the clonal outgrowth of a tumor (Ponta et al., 1994 *BBA*, 1198:1–10; Berstein and Liotta, 1994 *Current Opt. In Oncology;* 6:106–13; Brattein et al., 1994 *Current Opt. In Oncology;* 6:477–81; Fidler and Ellis, 1994 *Cell*, 79:315–28). These mutant genes provide cancer cells with a selective growth advantage by promoting resistance to immune-based destruction, allowing disobeyance of cell cycle checkpoints that would normally induce apoptosis, facilitating growth factor/hormone-independent cell survival, supporting anchorage-independent survival metastasis, reducing dependence on oxygen and nutrients, and conferring resistance to cytotoxic anticancer drugs and radiation. Therefore, elucidation of the genes that cause genetic instability in cancer cells, as well as identification of the genes that are most susceptible to the alterations, represents a promising approach for development of new strategies for combating cancer and for its diagnosis at early stages of development.

A. Genomic Instability

Genomic instability in its broadest sense is a feature of virtually all neoplastic cells. In addition to the mutations and/or gene amplification that appear to be a prerequisite for the acquisition of a neoplastic phenotype, human cancers exhibit other markers of genomic instability, and in particular, a high degree of aneuploidy. Many studies have shown that aneuploidy is an almost invariant feature of cancer cells, and it has been argued by some that the emergence of aneuploid cells is necessary step during tumorigenesis. The functional link between genomic instability and cancer is strengthened by the existence of several "genetic instability" disorders of humans that are associated with a moderate to severe increase in the incidence of cancers. These disorders include ataxia telangiectasia (Gonzalez-del Angel, A. et al., 2000 *Am. J. Med. Genet.*, 90:252–4), Bloom's syndrome (Karow, J. K. et al., 2000 *Proc. Natl. Acad. Sci. USA*, 97:6504–8), Faconi anemia (Leteutre, F. et al., 1999 *Brit. J. Hematol.*, 105: 883–93), xeroderma pigmentosum, and Nijmegen breakage syndrome (Mathur, R. et al., 2000 *Indian Pediatr.* 37: 615–25), of all which are very rare and are inherited in a recessive manner. Analysis of the cells from such cancer prone individuals is clearly a potentially fruitful approach for delineating the genetic basis for instability in the genome. It is assumed that by identifying the underlying cause of genetic instability in these disorders, one can derive valuable information not only about the basis of particular genetic diseases, but also about the underlying causes of genomic instability in sporadic cancers in the general population.

Currently, methods and strategies for identifying the pathology of related genes include genetic analysis of hereditary diseases, cytological methods including analysis of chromosomal aberrations and segregation analysis, and molecular biology methods including comparative genomic hybridization, microsatellite analysis, differential screening, differential display, methods of gene fishing, transgenics, knockout animals and gene function analysis.

Genomic instability plays a leading role in tumor progression and formation of metastatic cancer. This process involves activation of oncogenes, rearrangement of chromosomes, karyotipic, genetic and epigenetic instability and amplification of genes (Hart and Saini, 1992 *Lancet*, 339:1453–61; Seshadri et al., 1989 *Int. J. Cancer*, 43:270–72). The metastatic process depends not only on transformation, but also on a chain of interactions between tumor cells with the host's cells and tissues (Ponta et al., 1994 *BBA*, 1198: 1–10; Berstein and Liotta, 1994 *Current Opt. In Oncolgy*, 6:106–13; Brattein et al., 1994 *Current Opt. In Oncolgy*, 6:77–81; Fidler and Ellis, 1994 *Cell*, 79:315–28). A series of experiments revealed that neoplastic transformation resulted in changes in expression of genes coding $Ca^{++}$ binding proteins from the S100 gene family (Ebralidze et al., 1989 *Gen. Dev.*, 3:1086–93; Schafer and Heizmann, 1996 *TIBS*, 21:134–40). Expression of genes encoding metastasin (S100A4) (Ebralidze et al., 1989 *Gen. Dev.*, 3:1086–93), calcycline (S100A6) (Tomasetto et al., 1995 *Genomics*, 28:367–76), psoreasine (S100A7) and S100C (Moog-Lutz et al., 1995 *Int. J. Cancer*, 63:297–03) was enhanced, whereas expression of gene S100A2 was weakened (Lee et al., 1992 *Proc. Nat. Acad. Sci. USA*, 89:2504–08). It is hypothesized that these proteins participate in the tumor progression and metastasis through regulation of cell cycle and differentiation (Schafer and Heizman, 1996 *TIBS*, 21:134–40). The human protein metastasin-1, (hereinafter, "mts-1"), which is also referred to as its rodent homologue known also under the names of S100A4, calvasculin, cap1, p9ka, 42A, 18A2 and pEL98 as well the rodent homolog of the human protein has attracted attention from cancer researchers. The expression of mts-1 is observed in various aggressive cell strains (Baraclough et al., 1987 *J. Mol. Biol.*, 29:293–98; De Vouge and Mukerjee, 1992 *Oncogene*, 7:109–19). Moreover, it has been demonstrated that transfection of malignant rodent cell strains with the gene metastasin may enhance metastasis. (Grigorian et al., 1993 *Gene*, 135:229–38 and Davies et al., 1993 *Oncogene*, 8:999–1008). For example, when mouse embryonic fibroblasts were transfected with the scr gene, the rat homologue of mts-1, the protein pEL98 was co-localized on cytoskeleton elements identical with actin filaments and interacted with the heavy chain of non-muscular myosin.

Chromosome instability is a characteristic cytogenetic feature of a number of genetically determined disorders collectively referred to as the chromosome breakage syndrome or DNA repair disorders. These disorders are characterized by their increased susceptibility and frequency to chromosomal breakage and chromosome interchanges occurring either spontaneously or following exposure to various DNA damaging agents. These genetic disorders share a number of features. They are all autosomal recessive, demonstrate an increased tendency for chromosomal aberrations and development of malignancies. The principal diseases in this group, which have diverse etiologies and clinical manifestations, include Fanconi anemia (FA), ataxia telangiectasia (AT), Nijmegen breakage syndrome (NBS), Bloom syndrome (BS) (Karow, J. K. et al, *Proc Natl Acad. Sci. USA* 2000; 97: 6504–8), xeroderma pigmentosum (XP), Cockayne syndrome (CS) and trichothiodystrophy (TTD). The underlying defect in each of these syndromes is the inability to repair a particular type of DNA damage. A number of phenotypes are caused by more than one gene. The initial diagnosis of these syndromes is made by the characteristic clinical features specific to each disease, but the definitive diagnosis is achieved by laboratory investigations such as cytogenetic, biochemical and molecular methods.

B. Genetic Diseases

Multiple genetic alterations are commonly observed in human cancers and other genetic diseases as described below.

ICF Syndrome

ICF syndrome, characterized by immunodeficiency, centromeric region instability and facial anomalies is a unique DNA methylation deficiency disease diagnosed by chromosomal anomalies, especially in the vicinity of the centromeres of chromosomes 1 and 16 (Chr 1 and Chr 16) in mitogen-stimulated lymphocytes. These aberrations include decondensation of centromere-adjacent heterochromatin, (qh) multiradial chromosomes with up to 12 arms, and whole-arm deletions.

Bloom's Syndrome

Bloom's syndrome (BS) is a rare human autosomal recessive disorder characterized by an increased risk of developing all types of cancer. Cells of BS patients are characterized by a generalized genetic instability including a high level of sister chromatid exchanges. BS arises through mutations in both alleles of the BLM gene, which encodes a 3'→5' DNA helicase identified as a member of the RecQ family.

Werner Syndrome

Werner Syndrome (WS) is an autosomal recessive disease characterized by early onset of many features of aging, by an unusual spectrum of cancers and by genomic instability. The WS protein (WRN) possesses 3'→5' DNA helicase and associated ATPase activities, as well as 3'→5' DNA exonuclease activity.

Rothmund-Thomson Syndrome

Rothmund-Thomson Syndrome (RTS) is described in three isolated patients whose main features are bilateral radial aplasia, short stature, an inflammatory based 'elastic' pyloric stenosis, a pan-enteric inflammatory gut disorder that appears to be due to an autoimmune process, and poikiloderma. Other features in individual cases include cleft palate, micrognathia, and atresia, patellar aplasia/hypoplasia and sensorineural deafness. This combination may represent a severe form of RTS or possibly a previously unrecognized condition. Two kinds of RTS were recently shown to segregate for mutations in the human RECQL4 helicase gene.

Li—Fraumeni Syndrome

Li—Fraumeni Syndrome (LFS) is a rare familial multi-cancer syndrome characterized by the occurrence of sarcomas, breast cancer, brain tumors, leukemia, and adrenal cortical tumors in multiple relatives. In most cases, LPS is the result of inheritance of a mutant TP53 followed by somatic loss of the remaining wild-type allele, which constitutes the primary initiating event leading to cancer. (Sodha, N. et al., 2000 *Science,* 289: 359).

Fanconi Anemia

Fanconi Anemia (FA) is an autosomal genetic disease characterized by a complex array of developmental disorders, a high predisposition to bone marrow failure and to acute myelogenous leukemia. The chromosomal instability and hypersensitivity to DNA cross-linking agents led to its classification as a DNA repair disorder. (de Winter, J. P. et al., 1998 *JOURNAL* 8: 281–3). de Winter questioned whether it was appropriate to consider 1/approximately FA within a DNA repair framework in view of the recently discovered genetic heterogeneity characteristics of the defect (eight complementation groups). One possibility is that the FA proteins interact to form a complex which may control different functions, including the processing of specific DNA lesions. Such a complex may act as a sensor to initiate protective systems as well as transcription of specific genes specifying, among other proteins, growth factors. Such steps, may be organized as a linear cascade or more likely under the form of a web network.

Nijmegen Breakage Syndrome

Nijmegen Breakage Syndrome (NBS) is characterized by extreme radiation sensitivity, chromosomal instability and cancer. The phenotypes are similar to those of ataxia telangiectasia mutated (ATM) disease (Gonzalez-del Angel A., et al., 2000 *Am. J. Med. Genet.* 90: 252–4), in which there is a deficiency in a protein kinase that is activated by DNA damage, indicating that the Nbs and Atm proteins may participate in common pathways. Nbs is specifically phosphorylated in response to gamma radiation, ultraviolet light and exposure to hydroxyurea. Phosphorylation of Nbs mediated by gamma radiation, but not that induced by hydroxyurea or ultraviolet light was markedly reduced in ATM cells. In vivo, Nbs was phosphorylated on many serine residues of which S343, S397 and S615 were phosphorylated by Atm in vitro. At least two of these sites were underphosphorylated in ATM cells. Inactivation of these serines by mutation partially abrogated Atm-dependent phosphorylation. Reconstituting NBS cells with a mutant form of Nbs that cannot be phosphorylated at selected ATM-dependent serine residues led to a specific reduction in clonogenic survival after gamma radiation. Thus, phosphorylation of Nbs by Atm is critical for certain responses of human cells to DNA damage.

Ataxia-telangiectasia

The human neurodegenerative and cancer predisposition condition ataxia-telangiectasia (AT) is characterized at the cellular level by radiosensitivity, chromosomal instability, and impaired induction of ionizing radiation-induced cell cycle checkpoint controls. Recent work revealed that the gene defective in ataxia-telangiectasia, termed ATM, encodes an approximately 350 kilodalton (kDa) polypeptide. ATM is a member of the phosphatidylinositol 3-kinase family.

Cockayne Syndrome

Cockayne Syndrome (CS) is a human autosomal recessive disorder characterized by many neurological and developmental abnormalities. CS cells are defective in the transcription coupled repair (TCR) pathway that removes DNA damage from the transcribed strand of active genes. Individuals suffering from CS do not generally develop cancer but show increased neurodegeneration. (Senesen, M. et al., 2000 *Nucleic Acids Res.* 28: 3151–9).

Trichothiodystrophy

Trichothiodystrophy is an autosomal recessive genodermatosis associating congenital dysplasia of the hair and neuroectodermal defects. Clinical expression is variable, although abnormalities are generally noted from birth. The DNA repair-deficient genetic disorders, xeroderma pigmentosum (XP) and trichothiodystrophy (TTD) result from mutations in the XPD gene with different sites of mutation. Characteristics of XP are multiple pigmentation changes in the skin and a greatly elevated frequency of skin cancers. XPD and most TTD patients have reduced levels of DNA repair, but some reports have suggested that the repair deficiencies in TDD cells are milder than in XP-D cells.

SUMMARY OF INVENTION

The present invention describes a method for understanding the role of genomic instability in tumor progression and formation of metastatic cancer by identifying unstable genes associated with genetic instability. More specifically, the present invention involves a method for detecting genes associated in genetic alterations by using specific genes capable of inducing genetic instability such as mts-1 and their protein products.

The present inventors discovered that cells that were transfected with mts-1 and later expressed mts-1, resulted in acquired genomic instability. Based on this finding, the present invention provides a method for using the human mts-1 gene or its protein product, or their analogs, as well as other genes, their protein products and their analogs that have a similar function to that of mts-1 gene, to induce genetic instability in tissues and cell lines. Therefore, the present invention provides a method for detecting unstable genes by comparing the phenotype and gene expression pattern of subclones that express mts-1.

The present invention also provides a method for diagnosing and identifying genetic elements that are involved in a pathological process, as well as a tool for facilitating genome instability research. In addition, the present invention further provides a method for using these genetically induced unstable cell lines in kits for analysis of genome instability by genome dose variability array (GDVA).

DETAILED DESCRIPTION OF THE INVENTION

The present invention provides a method for identifying genes that are involved in genetic instability comprising the steps of transfecting cells with a vector expressing a gene capable of inducing genetic instability; selecting the cells that express the incorporated gene capable of inducing genetic instability; subcloning the cells; comparing the phenotypes of the subclones that express the incorporated gene capable of inducing genetic instability; and comparing the pattern of genetic expressions of the subclones. The present invention demonstrates that the mts-1 gene and its analogs and their protein products can be used to induce genome instability in stable cells and tissues.

Human breast carcinoma MCF7 cells were stably transfected with a vector expressing human mts-1. More importantly, the present invention demonstrates that genomic instability is induced by cells that express the mts-1 gene. In particular, selected MCF7 cell clones expressing mts-1 showed a remarkable variation in their phenotype in terms of their morphology, proliferation rate, sensitivity to estradiol and pattern of gene expression. Among the obtained cell clones, 40% demonstrated multilayer cell growth, indicating immortalization. After re-cloning, these cell strains showed a continued diversification of cell clones with respect to their phenotypes.

In a preferred embodiment, cells are transfected with a vector containing the human metastasin (mst-1) gene and its analogs and their protein products. Cells are selected for expression of mst-1 and subcloned to several generations and analyzed for diversity in phenotype and genetic expression patterns.

It was noted that in the subclones expressing mts-1, the proviral genome IAP (HERV-67) was eliminated whereas the pS2-gene was amplified. In addition, the pS2 and p53 genes, respectively showed a loss of correlation in a similar manner when compared to the dose of certain genes (i.e., uPA, TIMP-1, IAP and Bcl-x), whereas subclones of parental MCF7 cells and MOCK-transfected MCF7 control cells demonstrated a good internal correlation at comparisons between all genes. The loss of correlation between dose of different genes in mts-1-expressing cells indicates that mts-1 causes an unstable genome, which might explain the observed progressive diversification of phenotypes.

In another embodiment, patterns of genetic expression are analyzed using a known marker gene such as but not limited to the proviral genome IAP (HERV-67), uPA, TIMP-1, IAP, Bcl-x, p53 and pS2. Genomic DNA samples are isolated from clones, subclones, subpopulations of cells, solid tumors or from subpopulation of non-solid tumors in which genomic instability is induced by mts-1 gene or by its functional analogs. These samples may be labeled with dye or radioisotope, or any other tag known to one skilled in the art. The labeled samples are hybridized with different sets of cDNA, mRNA, oligonucleotide probes or non-coding DNA and RNA probes that are immobilized to an array. Commercial arrays can be used without limitation, such as Human Broad Coverage cDNA Microarray; Human Apoptosis; Human Cancer; Human Cell Cycle; Human Cell Interaction; Human Cytokine/Receptor; Human Hematology; Human Neurobiology; Human Oncogene/Tumor Suppressor; Human Stress; Human Cardiovascular; Human Trial Kit; Human Cancer 1.2; β-Kinase; β-Signal Transduction; β Metabolism; β Diagnostic expressed sequence tags; Human 1.2 I ; Human 1.2 II; Human Toxicology II; Human 1.2 III; Human Functional cDNA Microarray; Atlas Glass Human 1.0 Array; Mouse cDNA Broad Coverage MicroArray; Mouse Stress; Mouse 1.2; Mouse 1.2 II; Mouse 1.2 Cancer; Rat Stress; Rat 1.2; Rat 1.2 II; Rat Toxicology II; E. coli Gene Arrays; H. pylori Gene Arrays; B. subtilis Gene Arrays; H. Pylori ORFmers sets; B. subtilis ORFmer sets; E. coli ORFmer sets.

Further, the probe sets could be assembled using various sources such as, without limitation, cancer related genes, retroviral DNA or RNA, DNA fragments, cDNA and RNA extracted from various viruses, microorganisms, plants, insects and animals, synthetic oligonucleotides and their analogs or mimics. Analysis of instability is performed by calculating correlation coefficients (r) for each couple of probes, or by other statistical methods as described below.

In another embodiment, the genomic DNA samples are immobilized to an array and hybridized with sets of cDNA, mRNA, oligonucleotide probes, as well as non-coding DNA and RNA probes that are labeled with a dye or isotope, or any other tag. The probe sets could be assembled using various sources such as, without limitation, cancer related genes, retroviral DNA or RNA, DNA fragments, cDNA and RNA extracted from various viruses, microorganisms, plants, insects and other animals, synthetic oligonucleotides and their analogs and mimics. Analysis of instability is done by calculating correlation coefficients (r) for each couple or by other statistical methods as described below.

Analysis of instability can be performed by using statistical methods, for example, by calculating correlation coefficient (r) for each couple of genomic DNA samples. The following correlation analysis methods can be used without limitation: multiple regression; cluster analysis; factor analysis; classification trees; canonical analysis; multidimensional scaling; correspondence analysis; linear regression analysis.

In still another embodiment, analysis of genetic instability in the samples is performed by using comparative genomic hybridization; microsatellite analysis; differential display analysis; or any other similar methods that allow identification of genetic alterations.

In yet another embodiment, analysis of genetic instability of tumor tissues or other pathological tissues is preformed by comparing patterns of gene expression using two or more known marker genes. These marker genes may be identified by employing the method of this invention. Therefore, another embodiment of the present invention is a method for identifying unstable genes in cells that are involved in genomic instability comprising transfecting cells with a vector expressing human mts-1 or its functional analogs; selecting for the cells that express mts-1; subcloning the cells that express mts-1; comparing the phenotype of the subclones that express mts-1, comparing the pattern of gene expression of subclones with two or more marker genes; and identifying the cells as possessing unstable genes if the phenotype of the subclones that express mst-1 continues to demonstrate diversity and the pattern of gene expression for the subclones that express mst-1 show a loss of correlation with the marker gene when compared to other subclones that express mst-1. Genomic DNA, mRNA or cDNA isolated from samples obtained from the analyzed tissue samples are immobilized on arrays and hybridized with the marker genes that are labeled with radioactive or fluorescent probes or any other suitable tag. The correlation analysis between the doses of the marker genes in the samples is performed as described above. Such an analysis can be used without limitation for genetic diagnostics of the disease, evaluation of its development stage and its progression prognosis.

The results of the analysis generated from the present method can be used for evaluation of genetic instability of new genetically altered organisms and cell lines. In another embodiment a single gene or groups of genes that are identified by the above-described strategies, or their expression products are used as targets for therapeutic agents or for preparation of therapeutic and preventive vaccines against the disease.

In still another embodiment, genetic instability is stimulated ex vivo by using unstable genes of the present invention in tissue samples obtained from an individual patient to promote genetic alterations that are characteristics for disease progression in this particular individual. The single antigens or groups of antigens, or genetic material such as mRNA or cDNA, are further used to prepare therapeutic and preventive vaccines against the disease.

In another embodiment, the present invention can be used for diagnostics and identification of genetic elements involved in a pathological process related to genome instability.

EXAMPLES

Example I

Construction of mts-1 Expression Vectors

In order to facilitate subcloning, a mts-1 fragment was PCR-amplified using primers containing restriction sites. The pCMVmts-1 plasmid was obtained by inserting in the sense orientation, a 320 bp BamH1/Xba1fragment (nucleotides −10 to +310) into the pCMV vector in which expression is under the control of the cytomegalovirus (CMV) promoter (Baker et al., 1990).

A Tet-Off plasmid was obtained by inserting in the sense orientation, a 320 bp BamH1 fragment of mts-1 gene (nucleotides −10 to +310) into the pUHD10-3 which expression is under the control of the CMV minimal promoter which is under the tetracycline operator control.

A linear construct containing pCMV promoter, mts-1 gene, rabbit β-globin intron II and polyadenylation signal was obtained from pCMV mts-1 plasmid.

Genomic DNA fragment of mts-1 or cDNA of mts-1 can be used for insertion into the genome for stimulation of instability.

Example II

Preparation of Genetically Instable Cell Subclones

Malignant MCF7 cells (ATCC HTB 22) were cultured in plastic flasks in Eagle medium in modification by Dulbecco (DMEM), containing 10% of calf serum. The pCMVmts-1 plasmid was obtained by inserting in the sense orientation, a 320 bp BamHI/Xba1 mts1 cDNA into the pCMV vector in which expression is under the control of the CMV promoter (Baker et al., 1990). MCF7 cells were electroporated with a linearized pCMVmts-1 construct (10 ug) or linearized pCMV vector alone (10 ug), using a BioRad apparatus at 400 volts and 125 mF. Transfectants were then selected with the neomycin analog G418 (400 μg/ml, Gibco BRL) by means of the neomycin-resistance gene of the pCMV vector.

Cloning of MCF7 cells transfected by pCMV and pCMVmts-1 construction was performed in petri dishes (Falcon 100 mm) at the estimated density of 30 cells per dish. The visual control was performed under an inverted microscope (Nicon).

Total RNA was prepared from cultured cells using a single step procedure (Chomczynski and Sacchi, 1987). RNA was fractionated by electrophoresis on a 1% agarose gel in the presence of formaldehyde, and transferred to nylon membranes (Hybond N, Amersham). Filters were acidified for 10 min in 5% $CH_3COOH$ and stained for 10 min (0.004% methylene blue, 0.5M $CH_3COONa$, pH 5.0) prior to hybridization. Northern blots were hybridized under stringent conditions (50% formamide, 42° C.) with mts-1 fragment and 36B4 cDNA probes $^{32}$P-labeled by random priming. Washing was performed in 2×SSC, 0.1% SDS at 22° C., followed by 0.1×SSC, 0.1% SDS at 55° C.

The transgene expression was assayed using Western blot analysis. Confluent cells were trypsinized and centrifuged at 500 g for 5 min; at 20° C. Cell pellets were washed in PBS buffer and analyzed by SDS-polyacrylamide gel electrophoresis (15%) under reducing conditions. Protein concentration was determined using the BioRad kit (BioRad Laboratories). For immunoblot analysis, proteins were transferred after electrophoresis to nitrocellulose filters that were incubated with a mouse monoclonal antibody specific for human mts-1 (a generous gift from Dr. Lukanidin). Bound antibodies were visualized using a peroxidase-labeled goat antibody raised against mouse IgM, followed by Enhanced Chemiluminescence detection (ECL kit, Dupont NEN).

Among forty-eight primary cell clones with G418 resistance, eighteen clones were found to express mts-1 RNA and protein, whereas mts1 RNA and the protein were not detectable in the parental MCF7 cells, in the pCMV3 and pCMV4 clones transfected with the pCMV vector alone or in the pCMVmts-1 transfected clone 28A6.

Example III
Characterization of the Primary mts-1 Positive Cell Clones

The original MCF7 cells and the obtained cell clones were grown in 6-wells falcon plates with or without estradiol in DMEM medium supplemented with 10% FCS without the "phenol red". To remove estradiol and other steroids, the culture medium was treated with activated charcoal. The proliferation rates of the cells were analyzed by counting trypsinized cells every 24 hours using a Coulter cell counter (Coultronics, France). Cell proliferation was estimated as the ratio of the number of cells growing for 24 hr to the number of cells at the beginning of the experiment. The cell motility was analyzed using the "wound" test. To that end, a 1×10 mm parafilm bands were placed on the bottom of each well of 6-wells falcon plate, pressed down, and the analyzed cell suspensions were added. After the cells reach confluence the parafilm bands were removed, whereby allowing a cell-free space in the wells. The starting time point was the moment the parafilm bands were remove. The cell motility rates were measured using the following formula: $V=a(1_1-1_2)/2N$, where V is the monolayer border motility ($\mu$m/24 hr); $1_1$—the distance between borders of the monolayer at the beginning of the experiment; $1_2$—the distance between the right and the left monolayer borders in N days; a—proportionality coefficient measured experimentally using an internal standard scale bar. The results are presented in Table 1.

TABLE 1

Phenotypic characterization of the primary cell clones

| Clone (Mts-1 expression) | Proliferation Index | | Cell Motility, $\mu$m/day |
|---|---|---|---|
| | Estradiol + | Estradiol − | |
| 15A5 (+) | 1.69 | 1.38 | 113 ± 12 |
| 15B2 (+) | 1.45 | 0.96 | 250 ± 31 |
| 28A1 (+) | 1.26 | 1.00 | 18 ± 24 |
| 28B6 (+) | 1.11 | 0.80 | 98 ± 9 |
| 28A6 (−) | 1.55 | 0.99 | 64 ± 6 |
| MCF7 (−) | 1.61 | 1.00 | 112 ± 13 |

In addition to the above experiments, a visual observation on the cell growth and phenotype was performed by means of daily photographing of the same group of cells. A multilayer cell growth was observed in 40% of cases of mts-1 transfectants, but not in control clones,. The initial MCF7 cell line did not show multi-layer growth during the culturing.

Example IV
Subcloning of the Primary mts-1 Positive Clones

The primary cell clones of the Example I were subcloned further. The subclones that were obtained after the third subcloning demonstrated a high morphological diversity indicating a progressive change in phenotype within each obtained cell subclone expressing mts-1. The morphological variations in the subclones were represented by different colony sizes ranging from several cells to several hundred cells in one colony after two weeks of growth; different colony shapes and different cell sizes. Some colonies demonstrated internal heterogeneity such as several different cell shapes within a single colony. Universal feature observed for all subclones expressing mts-1 was an overgrowth of fillapodies, which was not observed in the parental MCF7 cells.

To confirm that the cells present in the same subclone are generated from the single parental primary clone, the location of the mts-1 insertion in the genome was analyzed. The cells from each subclone were grown in 75 mm$^2$ flasks to a confluent monolayer and washed twice with PBS. After the addition of 2 ml of buffer for genomic DNA extraction containing 10 mM Tris-HCl, pH 8.0; 0.1M Na$_2$-EDTA, pH 8.0; 0.5% SDS; 20 $\mu$g/ml ribonuclease A; 100 $\mu$g/ml proteinase K, the flasks were incubated at 56° C. for 12 hours. The genomic DNA was precipitated with 1 volume of isopropanol. After washing with 70% ethanol, DNA was dried in the air and dissolved in TE buffer at 4° C. For determination of the insertion localization, 10 $\mu$g genomic DNA from each sample were treated with endonuclease XhoI. For the control of the restriction completeness, 1 $\mu$g $\lambda$-phage DNA was added to the reaction mixture. DNA fractionation was performed in 0.8% agarose with subsequent transfer onto Hybond N$^+$ followed by hybridization with mts1 cDNA. The resulted Southern blot analysis confirmed that the insertion sites within the analyzed subclones were the same. Therefore, the subclones represent pure cell strains and are not a result of contamination by other transfectants.

Example V

Analysis of the Gene Doses of the Selected Gene Panel in the Cell Subclones

The following genes were analyzed in the subclones of the Example III: Cadherin, Bcl-x, PUMP-1, 36B4, Col72, uPA, pS2, mts1, p53, pS2, HERV-67. The same gene panel was analyzed in the cell subclones derived from the non-transfected MCF-7 cells and MCF-7 cells transfected with the MOCK plasmid without Mts-1 insert as control.

Cells were grown in 75 mm$^2$ flasks to a confluent monolayer and washed twice with PBSx1. After addition of 2 ml of buffer for extraction (10 mM Tris-HCl, pH 8.0; 0.1M Na$_2$-EDTA, pH 8.0; 0.5% SDS; 20 $\mu$g/ml ribonuclease A; 100 $\mu$g/ml proteinase K), the flasks were incubated at 42° C. for 12 hours. The genomic DNA was precipitated with 1 volume of isopropanol. After washing in 70% ethanol, DNA was dried in the air and dissolved in TE buffer at 4° C. For dot blot analysis, 10 $\mu$g genomic DNA was denatured in 0.4 M NaOH at 65° C. for 1 hour and deposited on 10 identical Hibond N$^+$ blots, 1 $\mu$g on each. The quantitative estimation of hybridization was carried out using a phosphoimager.

Southern dot blot analysis of the obtained subclones and of control subclones of MOCK-transformed MCF7 cell subclones was performed. We prepared 9 identical 96 wells-dot blots with immobilized DNA from subclones expressing and not expressing mts-1. As a control, genome DNA from BALB/c mouse and plasmid DNA containing Cadherin, Bcl-x, PUMP-1, 36B4, Col72, uPA, pS2, mts1, p53, pS2, HERV-67 genes were used. The dot blots were hybridized to the following $^{32}$P-labeled cDNA probes: TIMP-1, IAP (HERV-67), mts1, pS2; E-Cadherin, 36B4, Bcl-x, p53, uPA. A quantitative estimation of hybridization signals was carried out using a phosphoroimager. The results were grouped as shown in Table 2.

TABLE 2

Results of the hybridization analysis (relative units)

A. Mts1 transfected MCF7 subclones

| Clone/gene | uPA | TIMP1 | PS2 | Mts1 | HERV | CADH | 36B4 | Bcl-x | P53 |
|---|---|---|---|---|---|---|---|---|---|
| C1 | 16 | 46 | 1472 | 18 | 29 | 107 | 90 | 12 | 17 |
| C2 | 14 | 44 | 2285 | 22 | 25 | 115 | 111 | 13 | 21 |
| C3 | 30 | 63 | 2362 | 21 | 30 | 179 | 150 | 14 | 23 |
| C4 | 13 | 60 | 2407 | 23 | 22 | 143 | 113 | 9 | 21 |
| C5 | 15 | 59 | 2497 | 33 | 27 | 157 | 136 | 10 | 22 |
| C6 | 17 | 61 | 2053 | 24 | 27 | 149 | 125 | 11 | 21 |
| C7 | 17 | 42 | 2166 | 21 | 19 | 114 | 105 | 13 | 18 |
| C8 | 16 | 47 | 2303 | 21 | 17 | 105 | 102 | 10 | 23 |
| C9 | 16 | 45 | 2038 | 25 | 19 | 123 | 126 | 11 | 20 |
| C10 | 14 | 45 | 1391 | 20 | 21 | 98 | 97 | 11 | 21 |
| C11 | 23 | 119 | 3122 | 52 | 65 | 197 | 183 | 15 | 25 |
| C12 | 14 | 59 | 683 | 15 | 37 | 70 | 75 | 10 | 15 |
| C13 | 15 | 58 | 556 | 12 | 50 | 67 | 78 | 11 | 14 |
| C14 | 13 | 41 | 931 | 15 | 33 | 83 | 87 | 11 | 16 |
| C15 | 14 | 48 | 1258 | 19 | 31 | 100 | 92 | 8 | 19 |
| C16 | 13 | 86 | 1030 | 17 | 47 | 98 | 89 | 9 | 18 |
| C17 | 13 | 94 | 1273 | 22 | 62 | 126 | 115 | 11 | 19 |
| C18 | 24 | 77 | 2250 | 40 | 38 | 211 | 138 | 15 | 21 |
| C19 | 20 | 71 | 1882 | 33 | 41 | 165 | 120 | 15 | 23 |
| C20 | 17 | 54 | 1128 | 27 | 26 | 135 | 83 | 11 | 17 |
| C21 | 23 | 87 | 2731 | 40 | 42 | 255 | 170 | 15 | 22 |
| C22 | 17 | 54 | 737 | 31 | 30 | 111 | 118 | 11 | 17 |
| C23 | 18 | 72 | 1488 | 35 | 42 | 98 | 93 | 14 | 19 |
| C24 | 16 | 59 | 565 | 25 | 43 | 118 | 126 | 12 | 16 |
| C25 | 16 | 55 | 1091 | 23 | 39 | 86 | 85 | 12 | 17 |
| C26 | 20 | 56 | 1188 | 32 | 42 | 189 | 163 | 11 | 22 |
| C27 | 18 | 56 | 1186 | 26 | 39 | 139 | 111 | 10 | 19 |
| C28 | 16 | 50 | 724 | 23 | 30 | 119 | 100 | 11 | 21 |
| C29 | 14 | 63 | 287 | 12 | 49 | 64 | 58 | 11 | 14 |
| C30 | 17 | 58 | 865 | 29 | 35 | 133 | 83 | 10 | 19 |
| C31 | 20 | 57 | 1463 | 31 | 41 | 122 | 115 | 9 | 17 |
| C32 | 19 | 60 | 867 | 27 | 51 | 108 | 107 | 14 | 15 |
| C33 | 18 | 57 | 869 | 26 | 44 | 102 | 138 | 12 | 16 |
| C34 | 24 | 55 | 117 | 9 | 39 | 76 | 40 | 9 | 9 |
| C35 | 15 | 54 | 467 | 20 | 45 | 78 | 101 | 14 | 14 |
| C36 | 15 | 56 | 1247 | 28 | 39 | 126 | 120 | 11 | 18 |
| C37 | 14 | 45 | 678 | 26 | 41 | 99 | 95 | 11 | 15 |
| C38 | 15 | 40 | 799 | 19 | 28 | 89 | 78 | 10 | 16 |
| C39 | 17 | 54 | 615 | 24 | 38 | 86 | 82 | 9 | 16 |
| C40 | 16 | 46 | 1816 | 24 | 25 | 120 | 88 | 9 | 19 |

B. MCF7 subclones

| Clone/gene | uPA | TIMP1 | PS2 | Mts1 | HERV | CADH | 36B4 | Bcl-x | P53 |
|---|---|---|---|---|---|---|---|---|---|
| C1 | 14 | 61 | 279 | 9 | 39 | 97 | 92 | 8 | 12 |
| C2 | 12 | 34 | 148 | 7 | 21 | 45 | 42 | 9 | 10 |
| C3 | 16 | 64 | 920 | 8 | 16 | 124 | 103 | 10 | 22 |
| C4 | 10 | 27 | 91 | 7 | 10 | 34 | 22 | 8 | 10 |
| C5 | 15 | 61 | 975 | 9 | 32 | 160 | 128 | 12 | 20 |
| C6 | 16 | 62 | 1389 | 8 | 30 | 131 | 126 | 12 | 22 |
| C7 | 16 | 54 | 1888 | 8 | 37 | 150 | 151 | 11 | 22 |
| C8 | 17 | 67 | 687 | 10 | 43 | 132 | 123 | 13 | 23 |

C. MOK transfected MCF7 subclones

| Clone/gene | UPA | TIMP1 | PS2 | Mts1 | HERV | CADH | 36B4 | Bcl-x | P53 |
|---|---|---|---|---|---|---|---|---|---|
| C1 | 18 | 56 | 684 | 9 | 37 | 156 | 137 | 11 | 21 |
| C2 | 17 | 60 | 292 | 9 | 45 | 133 | 123 | 12 | 21 |
| C3 | 18 | 54 | 766 | 9 | 38 | 133 | 115 | 9 | 21 |
| C4 | 18 | 54 | 687 | 9 | 35 | 127 | 126 | 11 | 22 |
| C5 | 16 | 53 | 604 | 9 | 41 | 156 | 91 | 9 | 21 |
| C6 | 14 | 57 | 464 | 9 | 42 | 133 | 75 | 8 | 21 |
| C7 | 14 | 69 | 460 | 9 | 34 | 122 | 82 | 9 | 17 |
| C8 | 19 | 60 | 678 | 8 | 36 | 137 | 113 | 11 | 19 |
| C9 | 20 | 62 | 1694 | 8 | 32 | 115 | 155 | 13 | 16 |
| C10 | 20 | 70 | 1745 | 9 | 37 | 161 | 132 | 11 | 19 |

Example VI
Linear Regression Analysis of Results of Example V

The hybridization data of the Example IV were subjected to a linear regression statistical analysis. The resulted correlation coefficients (r) reflecting the relative doses of each couple of analyzed genes in the subclones are shown in tables 3–5. These results show that lack of correlation between the gene doses was observed only in the mts-1 transfected subclones (Table 3), while in the mts-1 negative subclones (MOCK transfected subclones, Table 5), as well as in the subclones derived from the parental MCF-7 cells (Table 4) all the analyzed gene doses were in correlation.

TABLE 3

Mts1 expressing MCF7 subclones*.

| TIMP | pS2 | mts1 | IAP | Cadh | 36B4 | Bclx | p53 | |
|---|---|---|---|---|---|---|---|---|
| 0.36 | 0.19 | 0.30 | 0.13 | 0.60 | 0.46 | 0.49 | 0.12 | uPA |
| | 0.22 | 0.50 | 0.75 | 0.52 | 0.49 | 0.41 | 0.23 | TIMP |
| | | 0.52 | −0.34 | 0.67 | 0.62 | 0.22 | 0.82 | pS2 |
| | | | 0.23 | 0.71 | 0.76 | 0.38 | 0.82 | mts1 |
| | | | | 0.09 | 0.09 | 0.27 | −0.28 | IAP |
| | | | | | 0.83 | 0.47 | 0.77 | Cadh |
| | | | | | | 0.52 | 0.70 | 36B4 |
| | | | | | | | 0.14 | Bclx |

TABLE 4

MCF7 cell subclones

| TIMP | pS2 | Mts1 | IAP | Cadh | 36B4 | Bclx | P53 | |
|---|---|---|---|---|---|---|---|---|
| 0.91 | 0.83 | 0.61 | 0.58 | 0.92 | 0.94 | 0.74 | 0.91 | UPA |
| | 0.58 | 0.50 | 0.61 | 0.86 | 0.84 | 0.58 | 0.76 | TIMP |
| | | | 0.49 | 0.84 | 0.90 | 0.81 | 0.90 | PS2 |
| | | | 0.74 | 0.73 | 0.67 | 0.35 | 0.42 | Mts1 |
| | | | | 0.63 | 0.72 | 0.37 | 0.32 | IAP |
| | | | | | 0.97 | 0.82 | 0.90 | Cadh |
| | | | | | | 0.79 | 0.88 | 36B4 |
| | | | | | | | 0.85 | Bclx |

TABLE 5

MCF7 MOCK transfected subclones.

| TIMP | pS2 | mts1 | IAP | Cadh | 36B4 | Bclx | p53 | |
|---|---|---|---|---|---|---|---|---|
| 0.64 | 0.87 | 0.64 | 0.60 | 0.70 | 0.85 | 0.65 | 0.67 | UPA |
| | 0.76 | 0.45 | 0.63 | 0.74 | 0.68 | 0.47 | 0.73 | TIMP |
| | | 0.55 | 0.50 | 0.89 | 0.84 | 0.80 | 0.79 | pS2 |
| | | | 0.49 | 0.59 | 0.26 | 0.59 | 0.36 | mts1 |
| | | | | 0.59 | 0.66 | 0.54 | 0.38 | IAP |
| | | | | | 0.78 | 0.46 | 0.80 | Cadh |
| | | | | | | 0.78 | 0.76 | 36B4 |
| | | | | | | | 0.69 | Bclx |

Example VII
Cluster Analysis of the Results Example V

The hybridization data of the Example V were subjected to cluster statistical analysis—(Squared Euclidian distances method). The following gene groups were established:
A: CADH; 36B4
B: TIMP; IAP
C: UPA; Mts-1; Bcl-x; p53
D: PS2

Example VIII
Cluster Analysis of the Results of Example V

The hybridization data of the Example 5 were subjected to clustering tree statistical analysis. The following gene groups were established:
A: CADH; 36B4
B: TIMP; IAP
C: UPA; Mts-1; Bcl-x; p53
D: PS2

Example IX
Preparation of p53 Plasmid Construct for Expression in Animal Tissues A p53 fragment was PCR-amplified using primers containing restriction sites in order to allow its subcloning. The pCMVmts-1 plasmid was obtained by inserting in the sense orientation, a 1.4 kb HindIII/Bgl II fragment into the pCMV vector in which expression is under the control of the cytomegalovirus (CMV) promoter.

Example X
Preparation of p53 Linear Construct for Expression in Animal Tissues A p53 fragment was PCR-amplified. Linear construction which expression is under the control of the cytomegalovirus (CMV) minimal promoter, intron II and polyadenylation signal of Rabbit β-globin was used for intramuscular immunization of mice.

Example XI
Preparation of p53 Adenoviral Construct for Expression in Animal Tissues A p53 fragment was PCR-amplified using primers containing restriction sites in order to allow its subcloning. The Adenovirus-mts-1 construction was obtained by inserting in the sense orientation, a 1.4 kb fragment into Adenovirus by using Adeno-X™ expression system (Clonetech).

Example XII
Protective Immunization of CT-26 Tumor Bearing Balb C Mice with the Plasmid Encoding p53

A plasmid (pCMV-p53) encoding p53 gene driven by the cytomegalovirus immediate early region promoter and enhancer was used for intramuscular immunization of mice implanted with CT-26 cells.

The plasmid was expanded in *E. coli* DH5α strain and prepared using a Qiagen Endotoxin-free plasmid Giga-prep kit according to the supplier's protocol. The purified plasmid DNA was resuspended in sterile saline (Gibco-BRL) and kept frozen in aliquots at a concentration of 5 mg/ml.

Before each intramuscular injection, the Balb C mice were anesthetized with a mixed solution of ketamine and xylazine. The animals were injected on days 0 and 14 with 5 and 50 ug of pCMV-p53. At day 20, each animal was challenged with $1 \times 10^6$ of CT-26 cells implanted subcutaneously and survival rates were monitored. The median survival times (MST) determined during this study were as follows: control group (non-immunized animals)–22.4±9 days; experimental group (immunized animals)–53±5.7 days.

This application incorporates by reference the following publications:

REFERENCES

1. Barraclough R, Savin J, Duble S K and Rudland P S: Molecular cloning and sequence of the gene for p9Ka, a cultured myoepitelial cell protein with strong homology to S100, a calcium-binding protein. 1987 *J Mol Biol* 198: 13–20.
2. Beaupain R, Prevost G, Mainguene C, Laine-Bidron C, Tambois A and Tambois E: Constitutious three-dimentional cultures of MCF7 cells in serum free medium. In Vitro 1993 *Cell Dev. Biol.;* 29: 293–98.

3. Bernstein L R, Liotta L A: Molecular mediators of interactions with extracellular matrix components in metastasis and angiogenesis. 1994 *Current Opinion in Oncology* 6:106–13.
4. Brattain M G, Howell G, Sun L, Willson J K V: Growth factor balance and tumor progression. 1994 *Current Opinion in Oncology* 6: 77–81.
5. Davies B R, Davies M P A, Gibbs F E M, Barrahlough R, Rudland P S: Induction of the metastatic phenotype by transfection of a benign rat mammary epithelial cell line with the gene for p9Ka, a rat calcium-binding protein, but not with the oncogene EJ-ras-1. 1993 *Oncogene* 8: 999–08.
6. Chomczynski P, Sacchi N. Single-step method of RNA isolation by acid guanidinium thiocyanate-phenol-chloroform extraction. 1987 *Anal Biochem.,* 162(1):156–9
7. de Winter J P, Waisfisz Q, Rooimans M A, van Berkel C G, Bosnoyanollins L, Alon N, Carreau M, Bender O, Demuth I, Schindler D, Pronk J C, Arwert F, Hoehn H, Digweed M, Buchwald M, Joenje H. The Fanconi anaemia group G gene FANCG is identical with XRCC9. 1998 *Nat Genet.,* 20(3):281–3.
8. De Vouge M W, Mukherjee B B: Transformation of normal rat kidney cells by v-K-ras enhances expression of transin 2 and an S-100-related calcium-binding protein. 1992 *Oncogene* 7: 109–19.
9. Ebralidze A, Tulchinsky E, Grigorian M, Afanasyeva A, Senin V, Revazova E, Lukanidin E: Isolation and characterization of a gene specifically expressed in different metastatic cells and whose deduced gene product has a high degree of homology to a Ca2+-binding protein family. 1989 *Gene Dev., 3:1086–93.*
10. Fidler I J and Ellis L M: The implications of angiogenesis for the biology and therapy of cancer metastasis. 1994 *Cell* 79: 315–28.
11. Gonzalez-del Angel A, Cervera M, Gomez L, Perez-Vera P, Orozco L, Carnevale A, Del Castillo V. Ataxia-pancytopenia syndrome. Jan. 31, 2000 *Am J Med Genet.,* 90(3):252–4.
12. Grigorian M S, Tulchinsky E, Zain S, Ebralidze A K, Kramerov D A, Kraijevska M V, Georgiev G P, Lukanidin E: The mts1 gene and control of tumor metastasis. 1993 *Gene* 135: 229–38.
13. Hart I R, Saini A: Biology of tumor metastasis. 1992 *Lancet* 339:1453–61.
14. Karow J K, Constantinou A, Li J L, West S C, Hickson I D. The Bloom's syndrome gene product promotes branch migration of holliday junctions. 2000 *Proc Natl Acad Sci USA.* 97(12):6504–8.
15. Lee S W, Tomasetto C, Swisshelm K, Keyomarsi K, Sager R: Down-regulation of a member of the S100 gene family in mammary carcinoma cells and reexpression by azadeoxycytidine treatment. 1992 *Proc Nat Acad Sci USA* 89: 2504–08.
16. Leteurtre F, Li X, Guardiola P, Le Roux G, Sergere J C, Richard P, Carosella E D, Gluckman E. Accelerated telomere shortening and telomerase activation in Fanconi's anaemia. 1999 *Br J Haematol.* 105(4):883–93.
17. Liotta L A, Steeg P S and Stetler-Stevenson W G: Cancer metastasis and angiogenesis: an Imbalance of positive and negative regulation. 1991 *Cell* 64:327–36.
18. Mathur R, Chowdhury M R, Singh G. Recent advances in chromosome breakage syndromes and their diagnosis. 2000 *Indian Pediatr.* 37(6):615–25. Review.
19. Moog-Lutz C, Bouillet P, Regnier C H, Tomasetto C, Mattei M G, Chenard M P, Anglard P, Rio M C, Basset P: Comparative expression of the Psoriasin (S100A7) and S100C genes in breast carcinoma and co-localization to human chromosome 1q21-q22. 1995 *Int J Cancer* 63: 297–03.
20. Ponta H, Sleeman J, Herrlich P: Tumor metastasis formation: cell-surface proteins confer metastasis-promoting or -suppressing properties. 1994 *BBA* 1198: 1–10. Schäfer B W and Heizmann W: The S100 family of EF-hand calcium-binding: proteins: functions and pathology. 1996 *TIBS* 21:134–40.
21. Seshadri R, Matthevws C, Dobrovic A and Horfall D J: The significace of oncogene amplification in primary breast cacer. 1989 *Int J Cancer* 43: 270–72.
22. Sodha N, Williams R, Mangion J, Bullock S L, Yuille M R, Eeles R A. Screening hCHK2 for mutations. 2000 *Science.* 289(5478):359.
23. Sunesen M, Selzer R R, Brosh R M, Balajee A S, Stevnsner T, Bohr V A. Molecular characterization of an acidic region deletion mutant of Cockayne syndrome group B protein. 2000 *Nucleic Acids Res.* 28(16):3151–9.
24. Tomasetto C, Regnier C H, Moog-Lutz C, Mattei M G, Chenard M P, Lidereau R, Basset P, Rio M C: Identification of novel human genes amplified and overexpressed in breast carcinoma and localized to the q11-q21.3 region of chromosome 17. 1995 *Genomics* 28: 367–76.

What is claimed is:

1. A method for identifying an unstable gene that is involved in genomic instability in cells, comprising the steps of:
   (a) transfecting the cells with a vector expressing human mts-1 or a functional analog thereof;
   (b) selecting for the transfected cells that express human mts-1 or the functional analog;
   (c) subcloning the cells resulting from step (b);
   (d) comparing the phenotypes of the subclones resulting from step (c);
   (e) determining a correlation coefficient for each gene in a gene panel by comparing the gene dosage of each gene in the gene panel with the gene dosage of a marker gene in genomic DNA isolated from the subclones; and
   (f) identifying a gene in the gene panel as an unstable gene if the phenotypes of the subclones demonstrate diversity and the correlation coefficient of the gene in the gene panel is less than 0.3.

2. A method for identifying an unstable gene that is involved in genomic instability in cells, comprising the steps of:
   (a) transfecting the cells with a vector expressing human mts-1 or a functional analog thereof, which vector expresses at least one other gene;
   (b) selecting for the transfected cells that express human mts-1 or the functional analog and which express the other gene;
   (c) subcloning the cells resulting from step (b);
   (d) comparing the phenotypes of the subclones resulting from step (c);
   (e) determining a correlation coefficient for each gene in a gene panel by comparing the gene dosage of each gene in the gene panel with the gene dosage of a marker gene in genomic DNA isolated from the subclones; and
   (f) identifying a gene in the gene panel as an unstable gene if the phenotypes of the subclones demonstrate diversity and the correlation coefficient of the gene in the gene panel is less than 0.3.

3. The method according to claim 1, wherein step (d) is performed by comparing morphology, proliferation rates and sensitivity to estradiol.

4. The method according to claim 1, wherein the marker gene is HERV-67, pS2, p53, uPA, TIMP-1, or Bcl-x.

5. The method according to claim 1, wherein the cells are breast carcinoma cells.

6. The method according to claim 2, wherein the other gene is a gene capable of inducing genetic instability.

* * * * *